US012364880B2

(12) United States Patent
Slayton

(10) Patent No.: US 12,364,880 B2
(45) Date of Patent: Jul. 22, 2025

(54) METHOD FOR MID-INTENSITY, NON-ABLATIVE ACOUSTIC TREATMENT OF INJURED TISSUE

(71) Applicant: Guided Therapy Systems, LLC, Scottsdale, AZ (US)

(72) Inventor: Michael H. Slayton, Phoenix, AZ (US)

(73) Assignee: Guided Therapy Systems, LLC, Scottsdale, AZ (US)

( * ) Notice: Subject to any disclaimer, the term of this patent is extended or adjusted under 35 U.S.C. 154(b) by 299 days.

(21) Appl. No.: 17/695,039

(22) Filed: Mar. 15, 2022

(65) Prior Publication Data

US 2022/0288425 A1 Sep. 15, 2022

Related U.S. Application Data

(60) Provisional application No. 63/161,252, filed on Mar. 15, 2021.

(51) Int. Cl.
*A61N 7/02* (2006.01)
*A61N 7/00* (2006.01)

(52) U.S. Cl.
CPC .............. *A61N 7/02* (2013.01); *A61N 7/00* (2013.01); *A61N 2007/0017* (2013.01); *A61N 2007/0056* (2013.01)

(58) Field of Classification Search
CPC .... A61N 2007/0013; A61N 2007/0017; A61N 2007/0026; A61N 2007/0034; A61N 7/02;
(Continued)

(56) References Cited

U.S. PATENT DOCUMENTS 6,575,956 B1 * 6/2003 Brisken ............. A61M 37/0092
604/500
9,149,658 B2 10/2015 Barthe et al.
(Continued)

FOREIGN PATENT DOCUMENTS

CN 109481011 A 3/2019
KR 20170020569 A * 2/2017 ............... A61N 7/00
(Continued)

OTHER PUBLICATIONS

"Ultrasound Therapy—StatPearls—NCBI Bookshelf." Web.archive. org, May 15, 2020, web.archive.org/web/20200515104544/https:/ www.ncbi.nlm.nih.gov/books/NBK547717/. Accessed Feb. 6, 2024. (Year: 2020).*
(Continued)

*Primary Examiner* — Sean D Mattson
(74) *Attorney, Agent, or Firm* — GTC Law Group PC & Affiliates

(57) ABSTRACT

A method for mid-intensity non-ablative acoustic treatment of injured tissue is disclosed. The method involves continuously moving an ultrasound probe across an extracorporeal skin surface while emitting non-ablative therapeutic ultrasound into the injured tissue in a non-ablative therapeutic ultrasound beam profile. The method terminates energy delivery if movement speed is below a speed threshold. The non-ablative therapeutic ultrasound beam profile provides substantially uniform heating throughout a treatment volume. The heating is non-ablative and triggers a healing response in the injured tissue.

20 Claims, 6 Drawing Sheets

(58) Field of Classification Search
CPC .............. A61N 7/00; A61N 2007/0056; A61N 2007/0082; A61N 2007/0091
See application file for complete search history.

(56) References Cited

U.S. PATENT DOCUMENTS

| | | | |
|---|---|---|---|
| 9,566,454 B2 * | 2/2017 | Barthe | ............... A61N 7/02 |
| 10,183,182 B2 | 1/2019 | Slayton et al. | |
| 10,974,079 B2 * | 4/2021 | Puleo | ............... A61N 7/00 |
| 2003/0093102 A1 * | 5/2003 | Cimino | ............... A61B 17/2202 |
| | | | 606/169 |
| 2004/0010222 A1 | 1/2004 | Nunomura et al. | |
| 2004/0097840 A1 * | 5/2004 | Holmer | ............ A61B 17/22012 |
| | | | 601/2 |
| 2006/0074355 A1 * | 4/2006 | Slayton | ............... A61N 7/02 |
| | | | 601/2 |
| 2007/0249046 A1 * | 10/2007 | Shields, Jr. | ........ A61H 23/0245 |
| | | | 601/2 |
| 2008/0269607 A1 * | 10/2008 | Ishida | ............... A61N 7/02 |
| | | | 600/439 |
| 2008/0294073 A1 | 11/2008 | Barthe et al. | |
| 2009/0093737 A1 | 4/2009 | Chomas et al. | |
| 2012/0165668 A1 * | 6/2012 | Slayton | ............... A61B 8/4254 |
| | | | 601/3 |
| 2012/0165848 A1 | 6/2012 | Slayton et al. | |
| 2013/0066237 A1 * | 3/2013 | Smotrich | ............ A61N 5/0619 |
| | | | 604/20 |
| 2015/0202468 A1 | 7/2015 | Slayton et al. | |
| 2015/0360058 A1 | 12/2015 | Barthe et al. | |
| 2016/0016015 A1 * | 1/2016 | Slayton | ............... A61H 23/0245 |
| | | | 601/3 |
| 2016/0375271 A1 | 12/2016 | Tsoref et al. | |
| 2018/0133470 A1 | 5/2018 | Park | |
| 2018/0296859 A1 * | 10/2018 | Guha | ............... A61K 31/395 |
| 2019/0009110 A1 * | 1/2019 | Gross | ............... A61N 7/00 |
| 2019/0151192 A1 | 5/2019 | Yamashita | |
| 2020/0069975 A1 | 3/2020 | Puleo et al. | |
| 2020/0164231 A1 * | 5/2020 | Cannata | ............... A61N 7/00 |
| 2020/0391051 A1 * | 12/2020 | Daly | ............... A61B 18/203 |
| 2022/0288426 A1 * | 9/2022 | Slayton | ............... A61N 5/025 |

FOREIGN PATENT DOCUMENTS

| | | | | |
|---|---|---|---|---|
| KR | 20190009734 A * | 1/2019 | ......... A61B 17/2251 |
| WO | 0204074 A1 | 1/2002 | |
| WO | WO-2012018386 A2 * | 2/2012 | ............. A61B 18/04 |
| WO | WO-2015192046 A1 * | 12/2015 | ......... A61B 18/1815 |
| WO | 2022197662 A2 | 9/2022 | |
| WO | 2022197663 A1 | 9/2022 | |
| WO | 2022197697 A1 | 9/2022 | |

OTHER PUBLICATIONS

Cheatham, Scott. "Therapeutic Modalities: Ultrasound." OccupationalTherapy.com, www.occupationaltherapy.com/articles/therapeutic-modalities-ultrasound-5366. (Year: 2020).*

International Search Report and Written Opinion for PCT/US2022/020321, mailed Jun. 29, 2022 (14 pages).

PCT/US2022/020320 , "International Application Serial No. PCT/US2022/020320, International Search Report and Written Opinion mailed Jun. 27, 2022", Guided Therapy Systems, LLC, 8 pages.

PCT/US2022/020320 , "International Application Serial No. PCT/US2022/020320, Preliminary Report on Patentability mailed Sep. 28, 2023", Guided Therapy Systems, LLC, 8 pages.

PCT/US2022/020321 , "International Application Serial No. PCT/US2022/020321, Preliminary Report on Patentability mailed Sep. 28, 2023", Guided Therapy Systems, LLC, 11 pages.

PCT/US2022/020376 , "International Application Serial No. PCT/US2022/020376, International Preliminary Report on Patentability mailed Sep. 28, 2023", Guided Therapy Systems, LLC, 9 pages.

PCT/US2022/020376 , "International Application Serial No. PCT/US2022/020376, International Search Report and Written Opinion mailed Jun. 8, 2022", Guided Therapy Systems, LLC, 4 pages.

* cited by examiner

METHOD FOR MID-INTENSITY, NON-ABLATIVE ACOUSTIC TREATMENT OF INJURED TISSUE

CROSS-REFERENCE TO RELATED APPLICATIONS

This application is related to, claims priority to, and incorporated by reference herein for all purposes U.S. Provisional Patent Application No. 63/161,252, filed Mar. 15, 2021.

BACKGROUND

Acoustic energy has traditionally been used in two ways for the treatment of muscles. First and oldest, low frequency acoustic energy has been used to provide mechanical action or "massage" to muscles. Second and more recently, focused ultrasound energy has been used to create small ablative lesions within muscles.

Low frequency acoustic energy applying the mechanical action of ultrasound to muscles has historically been non-effective. In addition to the mechanical action of ultrasound, there may have been a modest temperature increase associated with these treatments due to minor absorptions of acoustic energy. However, the thermal component of this treatment would traditionally involve temperature elevations of less than 0.1° C.

The use of focused ultrasound energy to create small ablative lesions within muscles has been recently shown to be a surprisingly efficacious treatment for muscle injuries. For example, U.S. Pat. No. 10,183,182 shows use of this approach for treating the historically difficult-to-treat condition of plantar fasciitis. Without wishing to be bound by any particular theory, the ablative lesions appear to trigger a healing cascade within the body. The healing cascade can be sufficient for healing the muscle injury. However, the use of focused ultrasound and the creation of ablative lesions does not come without risks. Specifically, the focused ultrasound used for these therapies is at a peak intensity that is intended to provide a controlled thermal injury in the form of an ablative lesion, so the treatment is inherently destructive and can provide unintended damage.

Hyperthermia is known for use in the field of medical ultrasound in two primary contexts: 1) ablative treatments; and 2) non-ablative cosmetic treatments. Ablative hyperthermia treatments are utilized to destroy unwanted tissues (for example, tumors) when the ablative lesions are adequately large to allow the macroscale destruction of tissue. Ablative hyperthermia treatments are utilized to initiate a healing response when the ablative lesions are adequately small to be fully healed by the initiated healing response. Non-ablative hyperthermia treatments are utilized in cosmetic applications, such as the treatment of acne.

A need exists in the art for a muscular treatment that is effective but does not include the potential downside associated with the use of high intensity focused ultrasound or the creation of ablative lesions.

SUMMARY

In an aspect, the present disclosure provides a method of treating injured tissue in a human subject. The injured tissue is located within a treatment volume. The treatment volume extends in a depth dimension relative to an extracorporeal skin surface between a proximal boundary depth and a distal boundary depth. The proximal boundary depth is at least 1 mm beneath the extracorporeal skin surface. The method includes: a) coupling a handheld ultrasound probe to the extracorporeal skin surface above the injured tissue; b) continuously moving the ultrasound probe along the extracorporeal skin surface in a movement pattern while the ultrasound probe is emitting a non-ablative therapeutic ultrasound beam profile into the injured tissue; and c) in response to sensing movement speed of the handheld ultrasound probe being below the speed threshold, terminating energy delivery from the ultrasound probe. The non-ablative therapeutic beam profile having a frequency, an unfocused, defocused, or weakly focused beam shape, and an intensity profile. The frequency is selected to provide substantially uniform heating between the proximal boundary depth and the distal boundary depth in view of selective absorption within the treatment volume and thermal diffusion properties of the treatment volume. The defocused beam shape has defocusing of between 0° and 45°. The weakly focused beam shape has an F number of 2 or greater. An average peak intensity is located between the proximal boundary depth and the distal boundary depth. The intensity profile and/or the average peak intensity is adapted to provide a non-ablative thermal profile when the non-ablative therapeutic ultrasound beam profile is active and the probe is moving above a speed threshold. Continuously applying the non-ablative therapeutic ultrasound beam profile to the treatment volume in the absence of movement and in the absence of a mechanism to terminate energy delivery would exceed an ablation threshold in at least a portion of the treatment volume. The continuously moving of step b) defines a lateral cross-sectional shape and size of the treatment volume. The lateral cross-sectional shape and size is substantially the same as an outline of the movement pattern. The lateral cross-sectional size is between 75% and 125% of a size of the movement pattern.

In another aspect, the present disclosure provides a method of treating injured tissue in a human subject. The injured tissue is located within a treatment volume. The treatment volume extends in a depth dimension relative to an extracorporeal skin surface between a proximal boundary depth and a distal boundary depth. The proximal boundary depth is at least 1 mm beneath the extracorporeal skin surface. The method includes: a) coupling a handheld ultrasound probe to the extracorporeal skin surface above the injured tissue; b) continuously moving the ultrasound probe along the extracorporeal skin surface in a movement pattern while the ultrasound probe is emitting a non-ablative therapeutic ultrasound beam profile into the injured tissue; and c) in response to sensing movement speed of the handheld ultrasound probe being below the speed threshold, terminating energy delivery from the ultrasound probe. The non-ablative therapeutic ultrasound beam profile has an unfocused, defocused, or weakly focused beam shape and an intensity profile. The weakly focused beam shape has an F number of 2 or greater. An average peak intensity is located between the proximal boundary depth and the distal boundary depth. The intensity profile is adapted to deposit energy into tissue in amounts that are balanced with frequency-dependent absorption properties, thermal equilibrating properties, and/or thermal diffusion properties of the tissue to provide substantially uniform sub-ablative heating within the target volume. The continuously moving of step b) defines a lateral cross-sectional shape and size of the treatment volume. The lateral cross-sectional shape and size is substantially the same as an outline of the movement pattern. The lateral cross-sectional size is between 75% and 125% of a size of the movement pattern.

In a further aspect, the present disclosure provides a method of treating injured tissue in a human subject. The injured tissue is located within a treatment volume. The treatment volume extends in a depth dimension relative to an extracorporeal skin surface between a proximal boundary depth and a distal boundary depth. The proximal boundary depth is at least 1 mm beneath the extracorporeal skin surface. The method includes: a) coupling a handheld ultrasound probe to the extracorporeal skin surface above the injured tissue; b) continuously moving the ultrasound probe along the extracorporeal skin surface in a movement pattern while the ultrasound probe is emitting a non-ablative therapeutic ultrasound beam profile into the injured tissue; and c) in response to sensing movement speed of the handheld ultrasound probe being below the speed threshold, terminating energy delivery from the ultrasound probe. The non-ablative therapeutic ultrasound beam profile has an unfocused, defocused, or weakly focused beam shape. The weakly focused beam shape has an F number of 2 or greater. An average peak intensity is located between the proximal boundary depth and the distal boundary depth. The intensity profile is adapted to thermally saturate the tissue within the treatment volume when the probe is moving above the speed threshold. The continuously moving of step b) defines a lateral cross-sectional shape and size of the treatment volume. The lateral cross-sectional shape and size is substantially the same as an outline of the movement pattern. The lateral cross-sectional size is between 75% and 125% of a size of the movement pattern.

BRIEF DESCRIPTIONS OF THE DRAWINGS

DETAILED DESCRIPTION

Figure 1:
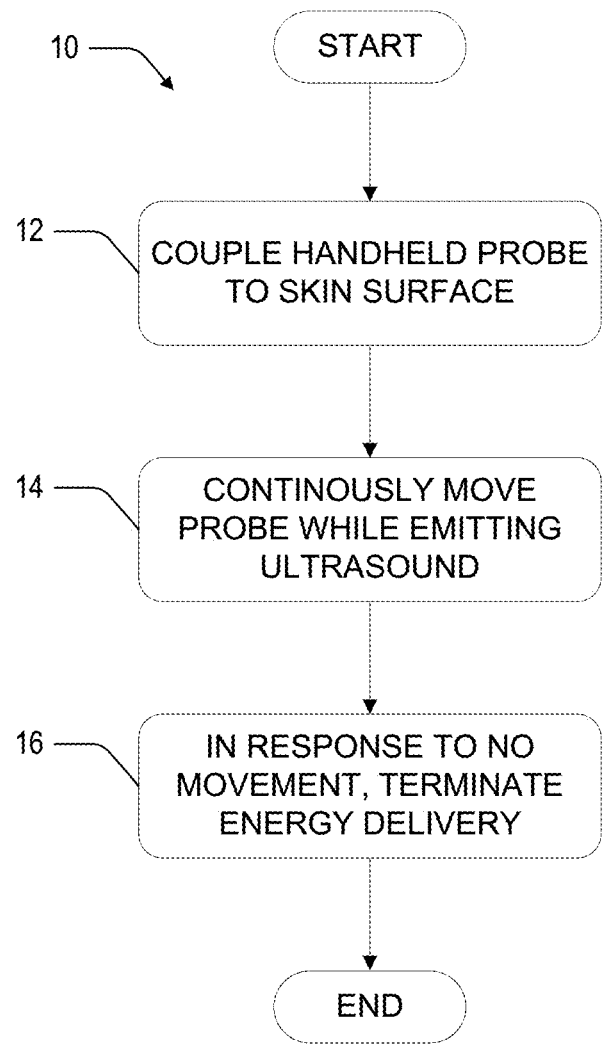
FIG. 1 is a flow chart of an exemplary method, according to one aspect of the present disclosure.

Before the present invention is described in further detail, it is to be understood that the invention is not limited to the particular embodiments described. It is also understood that the terminology used herein is for the purpose of describing particular embodiments only, and is not intended to be limiting. The scope of the present invention will be limited only by the claims. As used herein, the singular forms "a", "an", and "the" include plural embodiments unless the context clearly dictates otherwise.

Specific structures, devices and methods relating to ultrasound treatment and operation for the removal of a targeted tissue from a tissue of the body are disclosed. It should be apparent to those skilled in the art that many additional modifications beside those already described are possible without departing from the inventive concepts. In interpreting this disclosure, all terms should be interpreted in the broadest possible manner consistent with the context. Variations of the term "comprising" should be interpreted as referring to elements, components, or steps in a non-exclusive manner, so the referenced elements, components, or steps may be combined with other elements, components, or steps that are not expressly referenced. Embodiments referenced as "comprising" certain elements are also contemplated as "consisting essentially of" and "consisting of" those elements. When two or more ranges for a particular value are recited, this disclosure contemplates all combinations of the upper and lower bounds of those ranges that are not explicitly recited. For example, recitation of a value of between 1 and 10 or between 2 and 9 also contemplates a value of between 1 and 9 or between 2 and 10.

The various embodiments may be described herein in terms of various functional components and processing steps. It should be appreciated that such components and steps may be realized by any number of hardware components configured to perform the specified functions. For example, various embodiments may employ various cosmetic enhancement devices, visual imaging and display devices, input terminals and the like, which may carry out a variety of functions under the control of one or more control systems or other control devices. In addition, the embodiments may be practiced in any number of medical, non-medical, or cosmetic contexts and the various embodiments relating to a method and system for acoustic tissue treatment for removal of a targeted tissue from a tissue as described herein are merely indicative of some examples of the application for use in medical treatment or cosmetic enhancement. For example, the principles, features, and methods discussed may be applied to any medical, non-medical, or cosmetic application. Further, various aspects of the various embodiments may be suitably applied to medical, non-medical, or cosmetic applications for the skin, subcutaneous layers, or combinations thereof.

As used herein, the terms "ablation", "ablative", "ablative lesion", or variations thereof refer to thermal damage of tissue that is equivalent to or greater than the thermal damage produced by elevating the temperature of a tissue to 56° C. for one second. As used herein, the term "non-ablative" or variations thereof refer to thermal effects that do not reach the level of ablative effects. Each of these concepts can be described by reference to thermal dose, which is understood to those having ordinary skill in the art. Briefly, higher intensity doses applied for shorter lengths of time can achieve the same damage as lower intensity doses applied for longer lengths of time, and the concept of thermal dose encompasses all intensity and time doses that achieve the same damage as the given thermal dose. As one example, a thermal dose of 56° C. for a length of time of one second can be roughly equivalent to a thermal dose of 43° C. for a length of time of two hours. These relationships are not linear, but are well understood to those having ordinary skill in the acoustic arts.

As used herein, "proximal" and "distal" shall refer to orientation relative to an extracorporeal skin surface. Proximal is closer to the skin surface and distal is farther from the skin surface. "Above" may be used interchangeably with "proximal". "Below" may be used interchangeably with "distal".

This disclosure provides systems and methods for treating injured tissue. The systems and methods described herein are at least in part based on the surprising discovery that non-ablative thermal treatment of injured tissue can effectively treat tissue injury. Without wishing to be bound by any particular theory, it was previously believed that a thermal injury via creation of ablative lesions was necessary to provide a therapeutic benefit to injured tissue. As such, it was not believed that non-ablative thermal treatment was capable of being an effective treatment for injured tissue.

Referring to FIG. 1, a method 10 of treating injured tissue in a human subject is provided. The injured tissue is located within a treatment volume. The treatment volume extends in a depth dimension relative to an extracorporeal skin surface between a proximal boundary depth and a distal boundary depth. The proximal boundary depth is at least 1 mm beneath the extracorporeal skin surface. At process block 12, the method 10 includes coupling a handheld ultrasound probe to the extracorporeal skin surface above the injured tissue. The coupling can include applying a coupling gel to the extracorporeal skin surface. At process block 14, the method 10 includes continuously moving the ultrasound probe along the extracorporeal skin surface in a movement pattern while the ultrasound probe is emitting a non-ablative therapeutic ultrasound beam profile into the injured tissue. The non-ablative ultrasound beam profile has one or more of the characteristics described herein. The continuously moving of process block 14 defines a lateral cross-sectional shape and size of the treatment volume. The emitting of process block 14 is contingent upon the probe moving above a threshold movement speed. At process block 16, the method 10 includes, in response to sensing movement speed of the handheld ultrasound probe being below the speed threshold, terminating energy delivery from the ultrasound probe.

Figure 2:
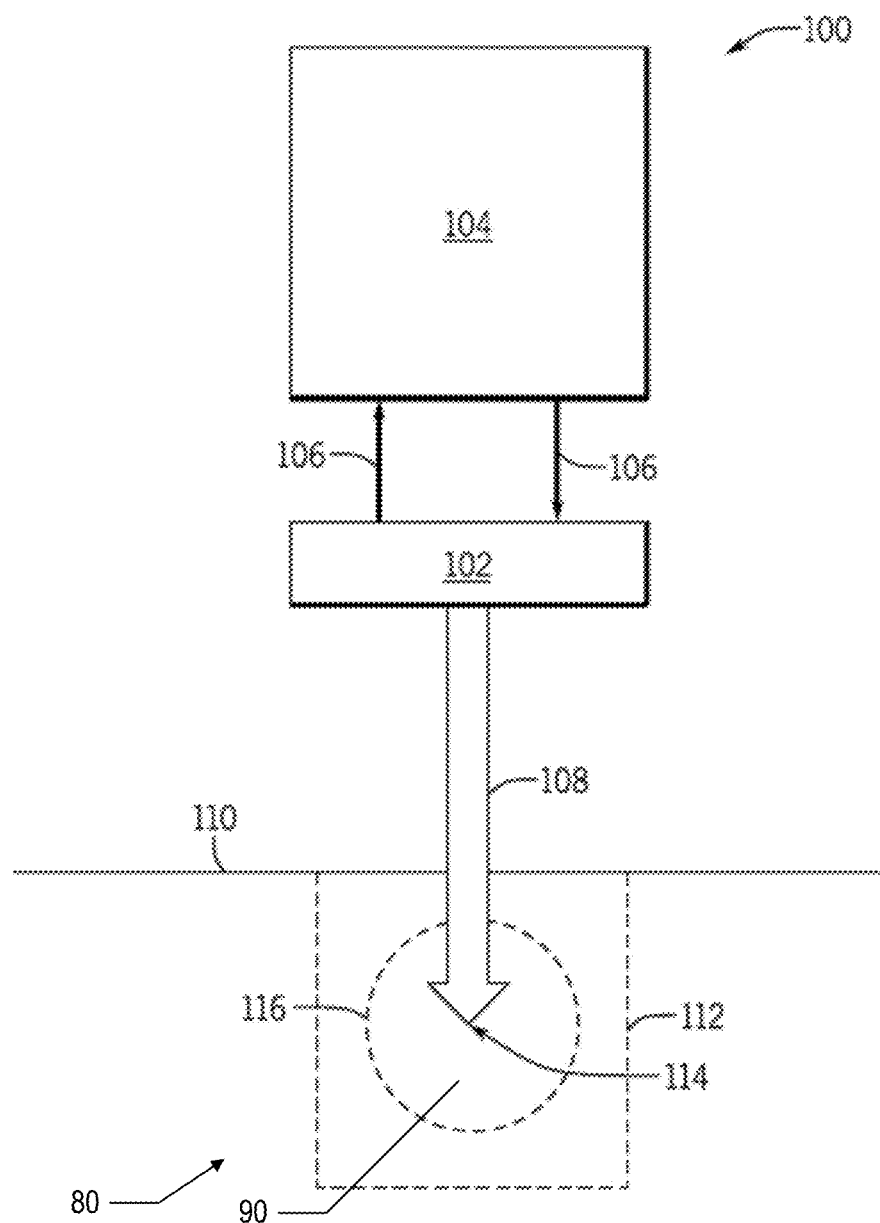
FIG. 2 is a block diagram illustrating an exemplary ultrasound delivery system, according to one aspect of the present disclosure.

Referring to FIG. 2, this disclosure provides an ultrasound delivery system 100. The ultrasound delivery system can include an ultrasound energy source 102 and a control system 104, which can be electronically coupled to one another via one or more communication conduits 106. The one or more communication conduits 106 can be wired or wireless. The ultrasound energy source 102 can be configured to emit ultrasound energy 108. The control system 104 can be configured to direct the ultrasound energy source 102 to emit ultrasound energy 108.

Still referring to FIG. 2, this disclosure provides systems and methods where the ultrasound energy source 102 can transmit ultrasound energy 108 across an optional boundary 110, such as a surface, and into a region of interest ("ROI") 112. The ultrasound energy 108 can be delivered to a target zone 114 within the ROI 112 containing at least part of injured muscle tissue 90. The ultrasound energy 108 can create an acoustic energy field 116 within the ROI 112. The ROI 112 or the target zone 114 can include injured muscle tissue 90, as described herein. The injured muscle tissue 90 is located within surrounding tissue 80.

In certain aspects, the ultrasound energy source 102 can be positioned within an ultrasound probe. The ultrasound probe can optionally be handheld. The control system 104 can be located within the ultrasound probe or remote from the ultrasound probe. The control system 104 or the system 100 can include a processor. The processor and/or control system 104 are adapted to execute the methods described herein.

Figure 3:
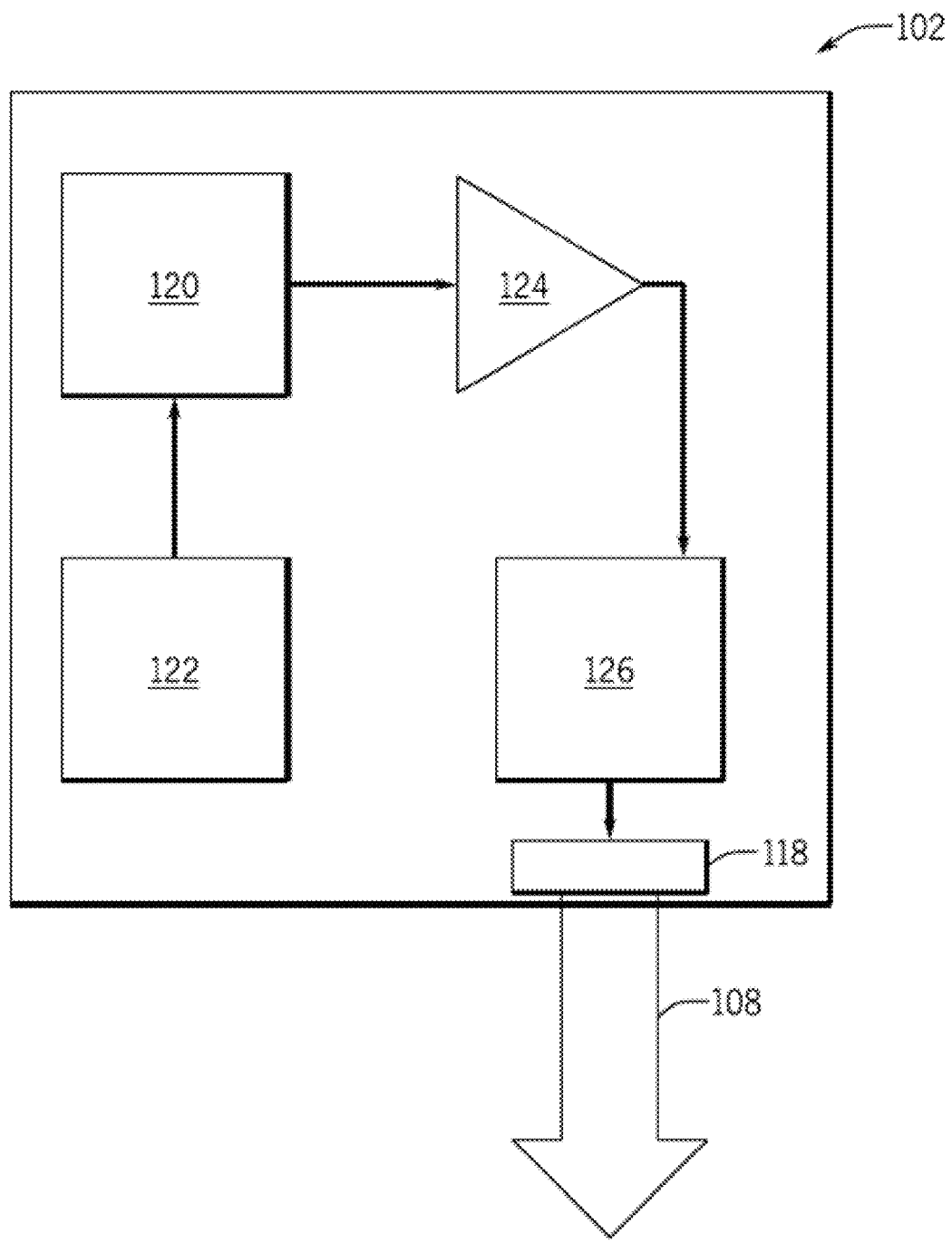
FIG. 3 is a block diagram of an exemplary ultrasound energy source, according to one aspect of the disclosure.

Referring to FIG. 3, the ultrasound energy source 102 can include a transducer 118, which is configured to emit ultrasound energy 108. The ultrasound energy source can further include a function generator 120, which can be powered by a power supply 122. The function generator 120 can be a radiofrequency ("RF") generator, a frequency generator, a pulse generator, a waveform generator, or a combination thereof. The power supply 122 can be located within the ultrasound energy source 102 or remote from the ultrasound energy source 102. The function generator can provide a drive signal to the transducer 118 that initiates the emission of ultrasound energy 108. The drive signal can have a drive frequency and a drive amplitude. The drive signal can be an RF signal. The ultrasound energy source 102 can optionally include an amplifier 124 that is configured to receive the drive signal, controllably amplify the drive signal to produce an amplified drive signal, and transmit the amplified drive signal to the transducer 118. The ultrasound energy source 102 can further optionally include an impedance matching network 126. The impedance matching network 126 can be configured to adjust the effective impedance or the load of the transducer 118 to match the impedance of the function generator 120 or the amplifier 124. The impedance matching network 126 can be configured to receive the drive signal from the function generator 120 and transmit a matched drive signal to the transducer 118 or to receive the amplified drive signal from the amplifier 124 and transmit a matched, amplified drive signal to the transducer 118.

In certain aspects, the ultrasound energy 108 can be continuous wave or pulsed. A person having ordinary skill in the acoustic arts will appreciate the ways in which either continuous wave or pulsed ultrasound energy can be utilized to achieve the non-ablative effects described herein.

In certain aspects, the ultrasound energy 108 can have a specific frequency. The ultrasound energy 108 can have a ultrasound frequency ranging from 2 MHz to 12 MHz including but not limited to, a ultrasound frequency ranging from 2 MHz to 5 MHz, from 2 MHz to 7 MHz, from 2 MHz to 10 MHz, from 3 MHz to 8 MHz, from 3 MHz to 11 MHz, from 4 MHz to 6 MHz, from 2 MHz to 10 MHz, from 5 MHz to 9 MHz, from 6 MHz to 12 MHz, from 7 MHz to 10 MHz, from 2 MHz to 4 MHz, from 3 MHz to 7 MHz, or combinations of the lower and upper bounds of those ranges which are not explicitly set forth.

In certain aspects, the ultrasound energy source 102 can be configured to deliver ultrasound energy 108 to the target zone 116 with an intensity loss relative to the intensity immediately after emission from the ultrasound energy source 102. The intensity loss can be in a range from 5 to 25,000, including but not limited to, a range from 1000 to 10,000. The intensity loss can be at least 500 or at least 1000.

In certain aspects, the ultrasound delivery system 100 can further include an ultrasound imager configured to image at least a portion of the ROI 112. The ultrasound imager can be located within the ultrasound probe or remote from the ultrasound probe. The ultrasound imager can be used, but is not limited to, in determining the depth or size of an injured muscle tissue 90 within the tissue 80. The ultrasound imager can be utilized as a remote temperature monitor, though a person having ordinary skill in the medical diagnostic arts would appreciate that other remote temperature monitors are possible.

In certain aspects, the ultrasound delivery system 100 can further include one or more additional ultrasound energy sources configured to deliver ultrasound energy to the ROI 112 or the injured muscle tissue 90. These one or more additional ultrasound energy sources can work independently to create independent non-ablative effects or can work constructively with the ultrasound energy source and other additional ultrasound energy sources to achieve the effects described herein.

In certain aspects, the ultrasound delivery system 100 can further include a secondary energy source configured to deliver a secondary energy to at least a portion of the ROI 112. The secondary energy source can be a photon-based energy source, an RF energy source, a microwave energy source, a plasma source, a magnetic resonance source, or a mechanical device capable of generating positive or negative pressures. Examples of a photon-based energy source include, but are not limited to, a laser, an intense pulsed light source, a light emitting diode, and the like. The secondary energy source can be located within the ultrasound probe or remote from the ultrasound probe. The secondary energy source can be configured to deliver the secondary energy before, during, or after the delivery of the ultrasound energy 108. In certain aspects, the ultrasound delivery system 100 can further include an energy sink configured to remove energy from the ROI 112, for example, by providing a cooling effect the ROI 112.

Figure 4:
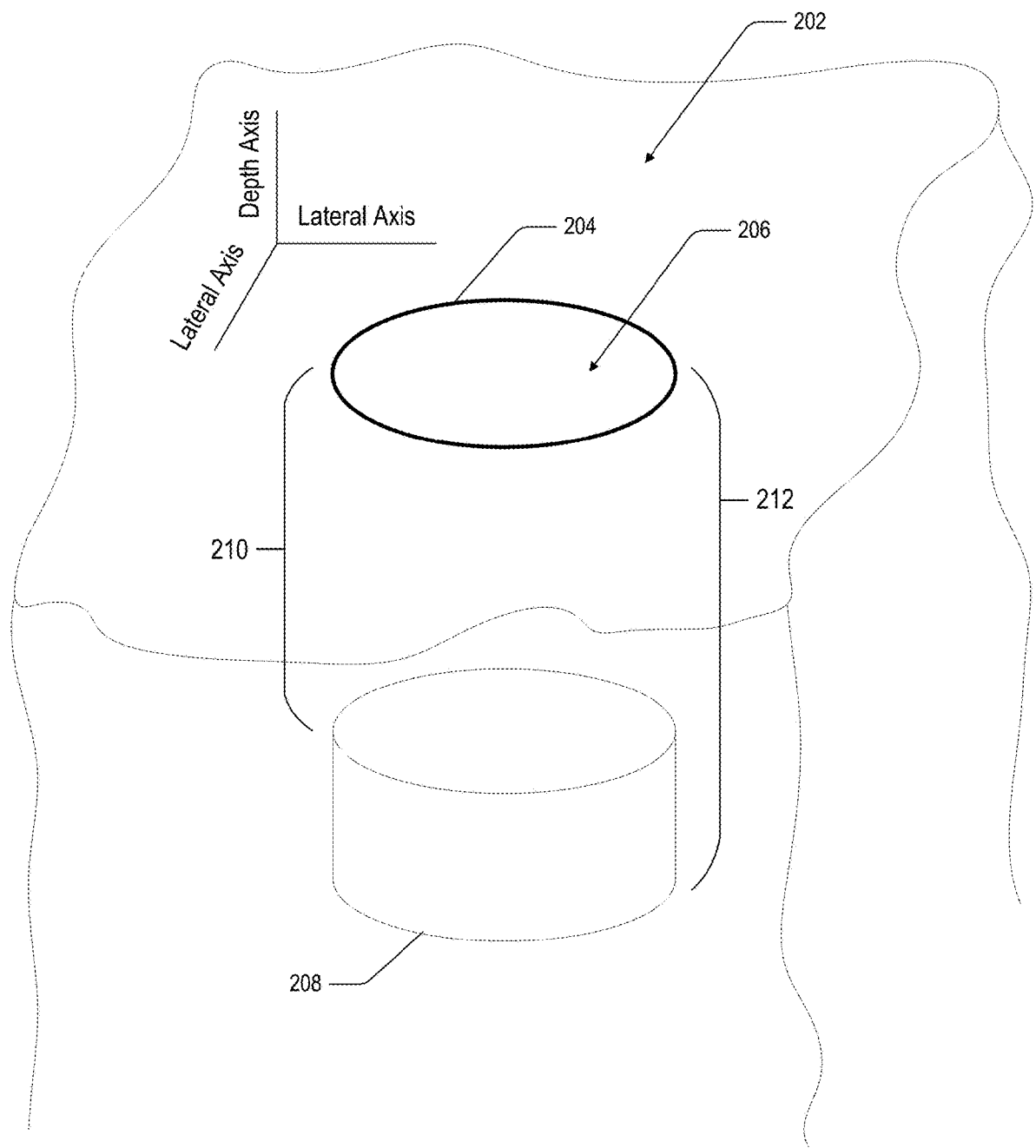
FIG. 4 is a diagram illustrating the geometry associated with the treatment volumes, in accordance with aspects of the present disclosure.

Referring to FIG. 4, a schematic of an extracorporeal skin surface 202 is illustrated. The ultrasound probe is moved on the surface 202 in a movement pattern having a movement pattern outline 204. The movement pattern outline 204 defines an internal area 206. Beneath the surface 202, the treatment volume 208 extends in a depth dimension relative to the surface 202 from a proximal boundary depth 210 to a distal boundary depth 212. The treatment volume 208 has a lateral cross-sectional shape and size. For ease of understanding only, the movement pattern outline 204 is illustrated as a circle (appears as an oval for perspective—the movement pattern 204 is in plane with the surface 202) and the treatment pattern 208 is illustrated as a cylinder—other shapes are expressly contemplated.

The lateral cross-sectional shape and size of the treatment volume is related to the movement pattern. The lateral cross-sectional shape is substantially the same as an outline of the movement pattern. As used herein, the substantial similarity of the outline of the movement pattern includes the size of the beam within the treatment volume. The lateral cross-sectional size is between 75% and 125% of a size of the movement pattern. In other words, the lateral cross-sectional size can be modestly larger or smaller than the movement pattern, depending largely on the beam shape and other beam characteristics.

The continuously moving of process block 14 can be done in a predetermined pattern, including but not limited to, a coil-shaped pattern (i.e., a pattern resembling the schematic symbol used for a spring in engineering drawings) or another pattern understood by those having ordinary skill in the art to provide useful coverage of the treatment volume.

One of the characteristics of the non-ablative therapeutic ultrasound beam profile is a frequency that is selected to provide substantially uniform heating between the proximal boundary depth and the distal boundary depth in view of selective absorption within the treatment volume and thermal diffusion properties of the treatment volume.

Another of the characteristics of the non-ablative therapeutic ultrasound beam profile is an unfocused, defocused, or weakly focused beam shape. The degree of defocusing can be between 0° and 45°. As used herein, the term "weakly focused" refers to ultrasound having an F number that is 2 or greater.

An additional characteristic of the non-ablative therapeutic ultrasound beam profile is an intensity profile having one or more of the properties described herein.

In some cases, the intensity profile has an average peak intensity that is located between the proximal boundary depth and the distal boundary depth (i.e., within the treatment volume).

In some cases, the intensity profile and/or the average peak intensity can be tuned such that the temperature in the treatment volume approaches the ablation threshold without exceeding it. This can be achieved by tuning the intensity profile and/or the average peak intensity to slightly exceed the ablation threshold in the absence of movement. To be clear, the systems and methods described herein prevent the emission of energy from the handheld ultrasound probe in the absence of movement, so this description of the intensity profile and/or the average peak intensity is describing what impact the non-ablative therapeutic ultrasound beam profile would have on tissue if the probe were not moving. Thus, the exceeding of the ablation threshold does not occur in operation, because energy delivery from the ultrasound probe is terminated (or never initiated) in response to sensing movement speed of the probe being below a speed threshold (including no movement). Without wishing to be bound by any particular theory, the intensities described herein are much higher than conventional unfocused ultrasound treatments, and one result of these higher intensities is reduced field homogeneity within the target volume. This reduced field homogeneity can provide spikes in intensity, which if they were to remain in a single location would results in a significant localized temperature increase. The continuously moving of the present disclosure, along with a roughly order of magnitude slower thermal response, causes a smoothing effect in the thermal distribution. Were the probe to remain motionless while the energy is emitted, ablation would occur. Intensity fluctuations throughout the treatment volume can be at least an order of magnitude greater than temperature fluctuations throughout the treatment volume.

In some cases, the intensity profile is adapted to deposit energy into tissue in amounts that are balanced with frequency-dependent absorption properties, thermal equilibrating properties, and/or thermal diffusion properties of the tissue to provide substantially uniform sub-ablative heating within the target volume.

In some cases, the intensity profile is adapted to thermally saturate the tissue (i.e., energy that would typically result in a temperature increase does not increase the temperature because it is balanced by thermal equilibration and/or thermal diffusion) within the treatment volume when the probe is moving above a speed threshold.

The intensity profile can be substantially consistent over time during use.

The non-ablative therapeutic ultrasound beam profile and/or the intensity profile can be adapted to denature at least a portion of proteins located in the treatment volume.

The non-ablative therapeutic ultrasound beam profile and/or the intensity profile can be adapted to establish a thermal equilibrium in the treatment volume when utilized in the treatment methods described herein.

The non-ablative therapeutic ultrasound beam profile can have a transition point that is adapted to be located at a depth beneath the extracorporeal skin surface of between 4 mm and 50 mm.

The transducer is adapted to produce the non-ablative therapeutic ultrasound beam profile having a frequency as describe above.

The ultrasound probe can be adapted to provide the non-ablative therapeutic ultrasound beam profile in pulses. The pulses can have a pulse energy of between 2 J and 10 J. The pulses can have a pulse power of between 10 W and 100 W. The pulses can have a pulse duration of between 10 ms and 500 ms. The pulses can have a pulse separation of between 10 ms and 500 ms.

The non-ablative therapeutic ultrasound beam profile and/or the intensity profile can have an average intensity of between 5 W/cm$^2$ and 500 W/cm$^2$.

In some cases, the beam profile and intensity can be adapted to allow treatment of areas that include nerves and bones without the typical risks associated with treating such areas using traditional high-intensity focused ultrasound. With respect to nerves, higher intensity ultrasound can cause sharp pain when striking a nerve or can even permanently damage nerves. The intensity profile of the therapeutic ultrasound beam of the present disclosure is tailored to prevent damage to nerves and to reduce or eliminate any sharp pains associated with treating areas including nerves. With respect to bones, the interface between soft tissue and bone is highly reflective, because of the acoustic impedance mismatch between the materials. When high-intensity focused ultrasound is used, these reflections can direct higher intensity ultrasound to unintended locations. For example, if an ultrasound beam is intended to be focused to a depth of 10 mm, but that beam is reflected at a 90 degree angle after penetrating only 5 mm, then the focal point will be located at 5 mm, thereby causing damage in an unintended location. It should be appreciated that these features relating to nerves and bones are generally true regarding unfocused and defocused ultrasound treatments, because of their general intensity profiles, but being able to achieve the thermal treatment described herein while also having the safety relative to nerves and bones described herein is impressive. Conventionally, achieving thermal treatments at depths beneath the skin surface has required careful tracking and avoidance of nerves and bones, but the inventors surprisingly discovered how to achieve thermal treatments at depth and without requiring the expense and complexity associate with tracking nerves and bones. As a result, the methods described herein can expressly exclude any steps of locating and/or monitoring bones and/or nerves.

Applicant appreciates that this mode of operation provides conditions where proper treatment may not be achieved. One example of this would be a user attempting to treat too large of an area/volume and/or moves the probe too fast. In this case, the thermal buildup of the ultrasound treatment may not high enough to achieve a therapeutic effect, but failing to achieve the desired therapeutic effect is not itself dangerous, so this risk is the kind of risk that is best mitigated by an end user. In other words, the device will operate safely regardless of how the end user applies the treatment, but improper treatment may be ineffective, but will remain safe.

In some aspects, the systems and methods described herein do not include features related to preventing undertreatment. In these cases, the prevention of undertreatment lies in the hands of the end user.

In some aspects, the systems and methods described herein do include features related to preventing undertreatment. Utilizing the motion sensors, the controller and/or processor can determine if the system is moving too fast and/or moving outside of a predetermined area (i.e., treating an area that is too large) and send a signal to an indicator, such as a light, a display, a haptic indicator, or the like. The indicator will provide to the user an indication that the user is operating the system in a fashion that is likely to result in undertreatment.

Broadly, it should be appreciated that the systems described therein are simpler than one could imagine for achieving the same or similar results. For instance, with the use of motion sensors, one could imagine increasing the intensity when the probe is moving faster and decreasing the intensity when the probe is moving slower, such that the average intensity per area remains relatively constant. Similarly, one can imagine real-time temperature monitoring to observe the temperature of the region of interest and using feedback to tailor ultrasound beam profile and intensity to provide a desired temperature increase. Applicant understands that more complicated systems could achieve the same outcomes as the systems and methods described herein. However, Applicant submits that at least some portion of the inventiveness in the present case results from the simplicity of the design and the ability to achieve this well-controlled mid-intensity thermal treatment with relatively inexpensive computational requirements.

In addition to the above-referenced aspects of the disclosure relating to how the system achieves the thermal treatment described herein, Applicant also submits that the therapeutic efficacy of the treatment itself is unexpected. There is no evidence in the literature that ultrasound treatment to nearly ablative, but non-ablative temperatures can provide a therapeutic healing effect to musculoskeletal injuries.

In some cases, the method 10 optionally includes: in response to a second predetermined length of time having lapsed following the terminating of process block 16 and/or in response to sensing movement speed of the handheld ultrasound probe being above the speed threshold, re-initiating the emitting of the non-ablative therapeutic ultrasound beam profile from the ultrasound probe. The second predetermined length of time can be at least 2 seconds, at least 3 seconds, at least 4 second, or at least 5 second, or at most 30 seconds, at most 20 seconds, at most 15 seconds, at most 10 seconds, or at most 7 seconds.

In some cases, the emitting the non-ablative therapeutic ultrasound beam profile of process block 14 can be programmed to occur for a predetermined length of time, such as between 10 seconds and 20 seconds. After that predetermined length of time, the method 10 can include terminating energy delivery from the handheld ultrasound probe.

As one practical consideration, the intensities of the non-ablative therapeutic ultrasound beam profile are higher than conventional non-ablative acoustic treatments, and the lifetime of the coupling medium is significantly shortened by these higher intensities. As a result, the method 10 can require re-applying the coupling medium to the extracorporeal skin surface between emissions. After re-applying the coupling medium, the delivery of the non-ablative therapeutic ultrasound can continue.

The method 10 can optionally include repeating the steps of process block 12 and 14 daily over the course of between 2 days and 28 days. This repeat treatment may be necessary to achieve a therapeutic effect.

The handheld ultrasound probe can include a transmission window that is adapted to defocus the ultrasound energy.

The handheld ultrasound probe can include a temperature sensor adapted to sense temperature within the handheld ultrasound probe.

The handheld ultrasound probe can include a flat transducer.

The desired time-temperature profile includes maintaining a temperature within a pre-defined temperature range for a pre-defined length of time. The pre-defined temperature range and the pre-defined length of time are selected to provide the desired non-ablative therapeutic effect.

The pre-defined temperature range can include a minimum temperature of at least 0.5° C., at least 1.0° C., at least 1.5° C., at least 2.0° C., at least 2.5° C., at least 3.0° C., at least 3.5° C., at least 4.0° C., at least 4.5° C., at least 5.0° C., at least 5.5° C., at least 6.0° C., at least 6.5° C., at least 7.0° C., at least 7.5° C., at least 8.0° C., at least 8.5° C., at least 9.0° C., at least 9.5° C., at least 10.0° C., at least 10.5° C., at least 11.0° C., at least 11.5° C., at least 12.0° C., at least 12.5° C., at least 13.0° C., at least 13.5° C., at least 14.0° C., at least 14.5° C., or at least 15.0° C. above body temperature. The pre-defined temperature range can have a maximum temperature of at most 16.0° C., at most 15.5° C., at most 15.0° C., at most 14.5° C., at most 14.0° C., at most 13.5° C., at most 13.0° C., at most 12.5° C., at most 12.0° C., at most 11.5° C., at most 11.0° C., at most 10.5° C., at most 10.0° C., at most 9.5° C., at most 9.0° C., at most 8.5° C., at most 8.0° C., at most 7.5° C., at most 7.0° C., at most 6.5° C., at most 6.0° C., at most 5.5° C., at most 5.0° C., at most 4.5° C., at most 4.0° C., at most 3.5° C., at most 3.0° C., at most 2.5° C., at most 2.0° C., at most 1.5° C., or at most 1.0° C. above body temperature.

The pre-defined length of time can be at least at least 2 seconds, at least 3 seconds, at least 4 second, or at least 5 second, and the pre-defined length of time is at most 30 seconds, at most 20 seconds, at most 15 seconds, at most 10 seconds, or at most 7 seconds.

In some cases, the method 10 involves elevating the temperature to a first temperature value, followed by a break in the treatment (optionally including re-applying the coupling gel), then elevating the temperature to a second temperature value, followed by a break in the treatment, then elevating the temperature to a third temperature value, followed by a break in the treatment, and repeating that process until the desired temperature is reached.

The method 10 can involve applying ultrasound in a burst of pulses, separated by a cooling period where coupling gel can be re-applied. The burst of pulses can include between 50 and 200 pulses. The pulses can have a repetition rate of between 3 Hz and 6 Hz. An individual treatment session can include 2, 3, 4, 5, 6, 7, 8, 9, 10, or more bursts of pulses.

The time-temperature profile for method 10 can be modeled and optimized with the aid of the thermal dose concept. The thermal dose, or $\tau_{43}$, is the exposure time at 43° C. which causes an equivalent biological effect due to an arbitrary time-temperature heating profile. Typically an ablative lesion forms on the order of one second at 56° C., which corresponds to a thermal dose of one hundred and twenty minutes at 43° C. The same thermal dose corresponds to 50° C. for approximately one minute. Thus, a non-ablative profile can contain high temperatures for very short times and/or lower temperatures for longer times or a combination of various time-temperature profiles. For example, temperatures as high as 56° C. for under one second or 46° C. for under fifteen minutes can be utilized. Such processes can be implemented in various exemplary embodiments, whereby one or more profiles may be combined into a single treatment.

The desired time-temperature profile can be adapted to provide an effective thermal dose that does not exceed an ablative thermal dose or 95%, 90%, 85%, 80%, 75%, or 50% of the ablative thermal dose at any time during the pre-defined length of time. The desired-time-temperature profile can be adapted to provide an effective thermal dose that does not exceed an equivalent of 120 minutes, 110 minutes, 100 minutes, 90 minutes, 80 minutes, 70 minutes, or 60 minutes at 43° C. at any point during the pre-defined length of time. In other words, the desired time-temperature profile can be adapted to ensure that ablation does not occur during the pre-defined length of time. In some cases, this is achieved by preventing effective thermal doses that are within a given percentage of an ablative thermal dose.

The ultrasound treatment plan that is optionally identified in process block 14 and that is used in process block 18 can include spatial and temporal parameters. With the desired time-temperature profile as a starting point, a person having ordinary skill in the therapeutic acoustic arts would appreciate how to determine the necessary spatial and temporal parameters to achieve the desired time-temperature profile in injured tissue of interest. It should be appreciated that there is not expected to be a single set of parameters to achieve a given time-temperature profile, but multiple different sets of spatial and temporal parameters can be utilized to achieve identical time-temperature profile. To put this another way, the invention in the present case does not relate to the technical ability to achieve a desired time-temperature profile in a given tissue (whether injured or not), but rather relates to a newly inventive medical treatment that utilizes ultrasound to achieve surprisingly effective healing for injured muscle tissue.

The method 10 can include cooling the extracorporeal surface, such as, for example, by use of an energy sink or a thermal sink, as would be appreciated by those having ordinary skill in the acoustic arts.

In some cases, the injured tissue is injured muscle tissue. As used herein, injured muscle tissue refers to muscle tissue that has been diagnosed with a muscle strain, a muscle tear, a muscle contusion, or a combination thereof.

In some cases, the injured tissue is an injured non-muscle soft tissue.

As used herein, a therapeutic effect refers to a reduction or elimination in the injury condition. In some cases, the therapeutic effect can refer to a reduction in the injury condition by at least 50%. In some cases, the therapeutic effect can refer to elimination of the injury condition. In some cases, the therapeutic effect is compared with the healing that occurs naturally in the absence of the inventive methods disclosed herein. It should be appreciated that therapeutic efficacy can be difficult to prove on a case-by-case basis, so therapeutic efficacy with respect to reduction or elimination of the injury condition may be established by traditional scientific methods, such as a double blind clinical trial.

The systems and methods disclosed herein can be useful for medical and non-medical applications. The systems and methods disclosed herein can be useful for non-invasive and/or non-surgical applications.

EXAMPLES

Example 1

2 MHz, 3 MHz, and 4 MHz probes were utilized to prove the concept of the systems and methods described herein.

For the 2 MHz and 3 MHz probes, the transducers were configured to produce pulses of ultrasound having a pulse power of 30 W, a pulse duration of 125 or 150 ms, a pulse repetition rate of 4 Hz. For the 4 MHz probe, the transducer was configured to produce pulses of ultrasound having a pulse power of 30 W, a pulse duration of 50 ms, and a pulse repetition rate of 4 Hz.

Treatment protocols involve the use of 400-500 overall pulses of ultrasound applied in batches with a cooling period in between the applications for the purpose of applying additional acoustic coupling gel to the surface. The batches of pulses can include 50-100 pulses.

A solidwater material was used to mimic the treatment volume. Thermal couples were placed at various depths in the material for measuring depth-dependent temperatures. Acoustic coupling gel was generously applied to the solid-water material and the handpiece was used to eliminate any air bubbles. Pulses of ultrasound were delivered normal to the surface and centered above the thermocouples. For the static experiments, the handpiece remained centered above the thermocouples. For the kinetic experiments, the handpiece was moved back and forth in a line above the thermocouples.

Tables 1, 2, and 3 show static depth-dependent temperature results for a 2 MHz, 3 MHz, and 4 MHz probe, respectively. All values have units of ° C. per second.

TABLE 1

2 MHz: Temperature Gradients

| | Power | | | | | | |
|---|---|---|---|---|---|---|---|
| | 30 W | | | | 25 W | | |
| | Pulse Length | | | | | | |
| | 150 ms | | 125 ms | | 150 ms | | 125 ms |
| | Frequency | | | | | | |
| | 3 Hz | 4 Hz | 3 Hz | 4 Hz | 3 Hz | 4 Hz | 4 Hz |
| 1 mm | 1.78 | 2.98 | 1.31 | 1.72 | 1.49 | 1.68 | 1.55 |
| 5 mm | 1.31 | 1.82 | 0.98 | 1.12 | 0.94 | 1.54 | 0.96 |
| 10 mm | 0.97 | 1.61 | 0.69 | 1.04 | 0.59 | 0.92 | 0.64 |
| 15 mm | 0.5 | 0.69 | 0.41 | 0.48 | 0.45 | 0.48 | 0.48 |

TABLE 2

3 MHz: Temperature Gradients

| Power | 30 W | |
|---|---|---|
| Pulse Length | 150 ms | 125 ms |
| Frequency | 4 Hz | 4 Hz |
| 1 mm | 2.58 | 2.7 |
| 5 mm | 2.46 | 2.06 |
| 10 mm | 1.79 | 1.25 |
| 15 mm | 0.64 | 0.54 |

TABLE 3

4 MHz: Temperature Gradients

| | Power | | | | | |
|---|---|---|---|---|---|---|
| | 20W | | 25W | | 30W | |
| | Pulse Length | | | | | |
| | 50 ms | | 50 ms | | 50 ms | |
| | Frequency | | | | | |
| | 3 Hz | 5 Hz | 4 Hz | 5 Hz | 4 Hz | 5 Hz |
| 1 mm | 0.84 | 1.37 | 1.17 | 1.21 | 0.78 | 1.7 |
| 5 mm | 0.57 | 0.92 | 0.75 | 0.92 | 0.68 | 1.22 |
| 10 mm | 0.39 | 0.71 | 0.67 | 0.64 | 0.78 | 1.2 |
| 15 mm | 0.1 | 0.3 | 0.17 | 0.18 | 0.23 | 0.24 |

Figure 5:
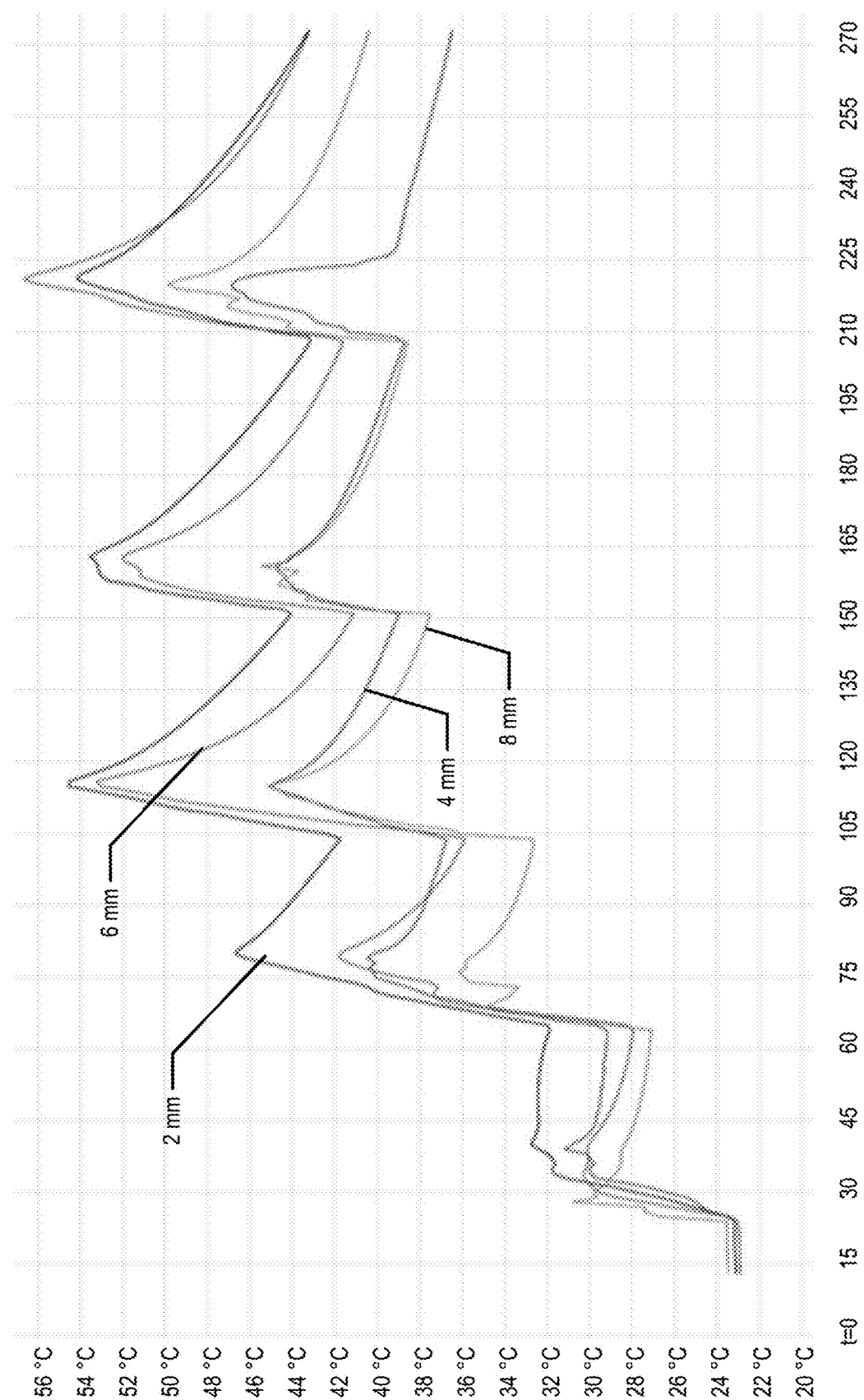
FIG. 5 is a data plot from kinetic testing in a solidwater model system, as described in Example 1.

Kinetic tests were performed with the same conditions as the static test and representative results are presented here. In one example of kinetic testing, with a 30 W power level and pulse length of 150 ms, about 25 pulses were needed to achieve a temperature increase of 15° C. Referring to FIG. 5, the time-variable temperature is plotted. Lines representing a 2 mm depth, a 4 mm depth, a 6 mm depth, and an 8 mm depth are labeled. The increases in temperature correspond to times when the ultrasound pulses are being transmitted and the decreases correspond to breaks in that transmission for the re-application of acoustic coupling gel. After the peak temperature is achieved, the treatment protocol continues to hit that temperature after applying each set of pulses. Note: the movement pattern is not the same movement pattern that would be recommended for a clinical application and the solidwater system does not have all of the thermal complexity of a clinical application, so the testing results are not intended to be representative of precisely what one would expect in a clinical application. Rather, these experiments serve as evidence that the general approach described above can be achieved and provides some surprising results.

Figure 6:
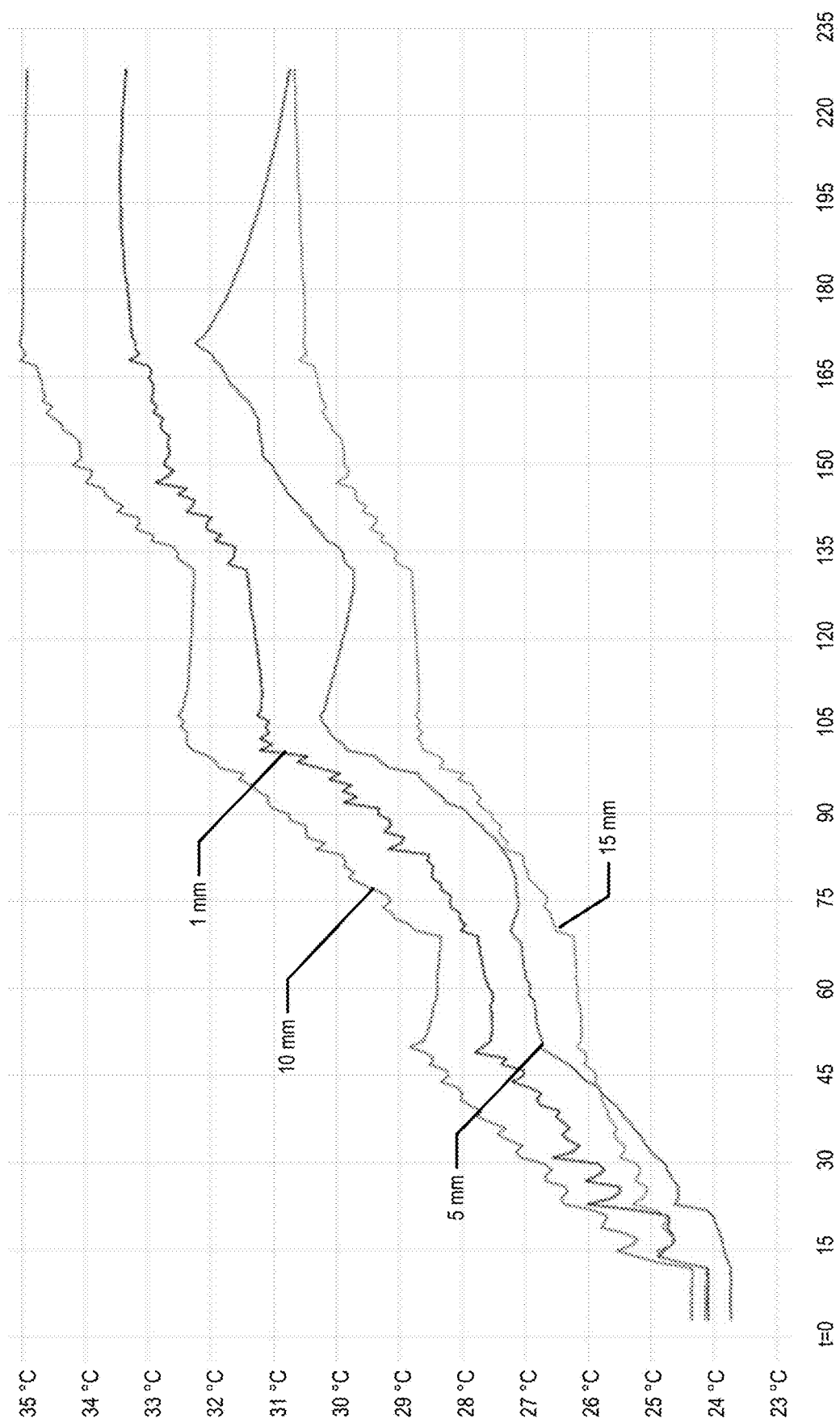
FIG. 6 is a data plot from kinetic testing in a pork loin model system, as described in Example 1.

Kinetic tests were also performed with the same conditions as the kinetic test of FIG. 5, but with a pork loin in place of the solidwater and with 100-150 pulses per interval with a 30 second break in between to re-apply coupling gel. Referring to FIG. 6, the time-variable temperature is plotted. Lines representing a 1 mm depth, a 5 mm depth, a 10 mm depth, and a 15 mm depth are labeled. The increases in temperature correspond to times when the ultrasound pulses are being transmitted and the decreases or plateaus correspond to breaks in that transmission for the re-application of acoustic coupling gel. It took roughly 400-500 pulses to achieve a 10° C. increase in the pork loin.

Example 2

The above-referenced parameters were used in testing on a shaved section of a subject's forearm to test pain induced by the treatment. A 3 MHz probe with power setting of 30 W, pulse length of 125 ms or 150 ms, and pulse repetition rate of 4 Hz and a 4 MHz probe with power setting of 30 W, pulse length of 50 ms, and pulse repetition rate of 4 Hz were used. After disabling the features described above with respect to preventing delivery when the probe is not moving, various deliveries were tested while hovering over a single spot and the general kinetic movement approaches described herein were utilized. During the hovering, heat buildup occurred quickly, but the quick buildup did not initiate a painful response. With kinetic movement, the treatment did not approach any pain threshold.

The present invention has been described above with reference to various exemplary configurations. However, those skilled in the art will recognize that changes and modifications may be made to the exemplary configurations without departing from the scope of the present invention. For example, the various operational steps, as well as the components for carrying out the operational steps, may be implemented in alternate ways depending upon the particular application or in consideration of any number of cost functions associated with the operation of the system, e.g., various of the steps may be deleted, modified, or combined with other steps. Further, it should be noted that while the method and system for ultrasound treatment as described above is suitable for use by a user proximate the patient, the system can also be accessed remotely, i.e., the user can view through a remote display having imaging information transmitted in various manners of communication, such as by satellite/wireless or by wired connections such as IP or digital cable networks and the like, and can direct a local practitioner as to the suitable placement for the transducer. Moreover, while the various exemplary embodiments may comprise non-invasive configurations, system can also be configured for at least some level of invasive treatment application. These and other changes or modifications are intended to be included within the scope of the present invention, as set forth in the following claims.

I claim:

1. A method of treating injured tissue in a human subject, wherein the injured tissue is located within a treatment volume, the treatment volume extending in a depth dimension relative to an extracorporeal skin surface between a proximal boundary depth and a distal boundary depth, wherein the proximal boundary depth is at least 1 mm beneath the extracorporeal skin surface, the method comprising:
 a) coupling a handheld ultrasound probe to the extracorporeal skin surface above the injured tissue;
 b) continuously moving the handheld ultrasound probe along the extracorporeal skin surface in a movement pattern while the handheld ultrasound probe is emitting a non-ablative therapeutic ultrasound beam profile into the injured tissue, the non-ablative therapeutic ultrasound beam profile having the following characteristics:
  a frequency selected to provide substantially uniform heating between the proximal boundary depth and the distal boundary depth in view of selective absorption within the treatment volume and thermal diffusion properties of the treatment volume;
  an unfocused, defocused, or weakly focused beam shape, the defocused beam shape having defocusing of between 0° and 45°, wherein the defocusing is measured as an angle relative to a propagation direction of the non-ablative therapeutic ultrasound beam profile, the weakly focused beam shape having an F number of 2 or greater; and
  an intensity profile, wherein an average peak intensity is located between the proximal boundary depth and the distal boundary depth, wherein the intensity profile and/or the average peak intensity is adapted to provide a non-ablative thermal profile when the non-ablative therapeutic ultrasound beam profile is active and the handheld ultrasound probe is moving above a speed threshold, wherein continuously applying the non-ablative therapeutic ultrasound beam profile to the treatment volume in an absence of movement and in an absence of a mechanism to terminate the energy delivery would exceed an ablation threshold in at least a portion of the treatment volume;
 c) in response to sensing movement speed of the handheld ultrasound probe being below the speed threshold, terminating energy delivery from the ultrasound probe, wherein the continuously moving of step b) defines a lateral cross-sectional shape and lateral cross-sectional size of the treatment volume, wherein the lateral cross-sectional shape is substantially the same as an outline of the movement pattern, wherein the lateral cross-sectional size is between 75% and 125% of a size of the outline of the movement pattern.

2. The method of claim 1, the method further comprising:
d) in response to a second predetermined length of time having lapsed following the terminating of step c) and/or in response to sensing the movement speed of the handheld ultrasound probe being above the speed threshold, re-initiating the emitting of the non-ablative therapeutic ultrasound beam profile from the handheld ultrasound probe.

3. The method of claim 2, wherein the second predetermined length of time is at least 2 seconds and at most 30 seconds.

4. The method of claim 1, wherein the intensity profile is substantially consistent over time during use.

5. The method of claim 1, wherein the emitting of the non-ablative therapeutic ultrasound beam profile of step b) occurs for a length of time between 10 seconds and 20 seconds, followed by terminating the energy delivery from the handheld ultrasound probe.

6. The method of claim 5, further comprising re-initiating the emitting of the non-ablative therapeutic ultrasound beam profile of step b) and/or repeating steps a) and b).

7. The method of claim 1, the method comprising repeating steps a) and b) daily over a course of between 2 days and 28 days, thereby providing a therapeutic healing effect.

8. The method of claim 1, wherein intensity fluctuations throughout the treatment volume are at least ten times greater than temperature fluctuations throughout the treatment volume.

9. The method of claim 1, wherein the speed threshold is between 0.5 cm/s and 10 cm/s.

10. The method of claim 1, wherein the ultrasound probe comprises a transmission window that defocuses the ultrasound energy.

11. The method of claim 1, wherein the ultrasound probe is adapted to provide the non-ablative therapeutic ultrasound beam in pulses having a pulse energy of between 2 J and 10 J.

12. The method of claim 1, wherein the ultrasound probe is adapted to provide the ultrasound energy in pulses having a pulse power of between 10 W and 100 W.

13. The method of claim 1, wherein the ultrasound probe is adapted to provide the ultrasound energy in pulses having a pulse duration of between 10 ms and 500 ms, a pulse separation of between 10 ms and 500 ms, or both.

14. The method of claim 1, the method comprising, applying a coupling medium to the extracorporeal skin surface prior to the coupling of step a).

15. The method of claim 14, the method further comprising, in response to the continuously moving of step b) occurring for a length of time of between 10 seconds and 15 seconds and/or for a length of time that causes at least a portion of the coupling medium to evaporate, re-applying the coupling medium to the extracorporeal surface and repeating steps a) and b).

16. The method of claim 1, wherein the method denatures at least a portion of proteins located in the treatment volume.

17. The method of claim 1, wherein the method establishes a thermal equilibrium in the treatment volume.

18. The method of claim 1, wherein the continuously moving of step b) includes moving in a coil-shaped pattern.

19. A method of treating injured tissue in a human subject, wherein the injured tissue is located within a treatment volume, the treatment volume extending in a depth dimension relative to an extracorporeal skin surface between a proximal boundary depth and a distal boundary depth, wherein the proximal boundary depth is at least 1 mm beneath the extracorporeal skin surface, the method comprising:
 a) coupling a handheld ultrasound probe to the extracorporeal skin surface above the injured tissue;
 b) continuously moving the handheld ultrasound probe along the extracorporeal skin surface in a movement pattern while the handheld ultrasound probe is emitting a non-ablative therapeutic ultrasound beam profile into the injured tissue, the non-ablative therapeutic ultrasound beam profile having the following characteristics:
  an unfocused, defocused, or weakly focused beam shape, the defocused beam shape having defocusing of between 0° and 45°, wherein the defocusing is measured as an angle relative to a propagation direction of the non-ablative therapeutic ultrasound beam profile, the weakly focused beam shape having an F number of 2 or greater; and
  an intensity profile, wherein an average peak intensity is located between the proximal boundary depth and the distal boundary depth, the intensity profile is adapted to deposit energy into tissue in amounts to provide substantially uniform sub-ablative heating within the treatment volume, c) in response to sensing movement speed of the handheld ultrasound probe being below a speed threshold, terminating energy delivery from the handheld ultrasound probe, wherein the continuously moving of step b) defines a lateral cross-sectional shape and a lateral cross-sectional size of the treatment volume, wherein the lateral cross-sectional shape is substantially the same as an outline of the movement pattern, wherein the lateral cross-sectional size is between 75% and 125% of a size of the outline of the movement pattern.

20. A method of treating injured tissue in a human subject, wherein the injured tissue is located within a treatment volume, the treatment volume extending in a depth dimension relative to an extracorporeal skin surface between a proximal boundary depth and a distal boundary depth, wherein the proximal boundary depth is at least 1 mm beneath the extracorporeal skin surface, the method comprising:

a) coupling a handheld ultrasound probe to the extracorporeal skin surface above the injured tissue;

b) continuously moving the handheld ultrasound probe along the extracorporeal skin surface while the handheld ultrasound probe is emitting a non-ablative therapeutic ultrasound beam profile into the injured tissue, the non-ablative therapeutic ultrasound beam profile having the following characteristics:

an unfocused, defocused, or weakly focused beam shape, the defocused beam shape having defocusing of between 0° and 45°, wherein the defocusing is measured as an angle relative to a propagation direction of the non-ablative therapeutic ultrasound beam profile, the weakly focused beam shape having an F number of 2 or greater; and an intensity profile, wherein an average peak intensity is located between the proximal boundary depth and the distal boundary depth, the intensity profile adapted to thermally saturate the injured tissue within the treatment volume when the handheld ultrasound probe is moving above a speed threshold, c) in response to sensing movement speed of the handheld ultrasound probe being below the speed threshold, terminating energy delivery from the handheld ultrasound probe, wherein the continuously moving of step b) defines a lateral cross-sectional shape and a lateral cross-sectional size of the treatment volume, wherein the lateral cross-sectional shape is substantially the same as an outline of a movement pattern, wherein the lateral cross-sectional size is between 75% and 125% of a size of the outline of the movement pattern.

* * * * *